(12) United States Patent
Govari et al.

(10) Patent No.: US 9,977,096 B2
(45) Date of Patent: May 22, 2018

(54) CONNECTOR WITH ACTIVE SHIELDING

(75) Inventors: Assaf Govari, Haifa (IL); Andres Claudio Altmann, Haifa (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 209 days.

(21) Appl. No.: 13/178,054

(22) Filed: Jul. 7, 2011

(65) Prior Publication Data

US 2013/0012808 A1     Jan. 10, 2013

(51) Int. Cl.
*A61B 5/05* (2006.01)
*G01R 33/025* (2006.01)
*A61B 5/06* (2006.01)

(52) U.S. Cl.
CPC ............ *G01R 33/025* (2013.01); *A61B 5/062* (2013.01)

(58) Field of Classification Search
CPC ............................. A61B 5/062; G01R 33/025
USPC ...................... 600/466; 439/39, 88
See application file for complete search history.

(56) References Cited

U.S. PATENT DOCUMENTS

| | | |
|---|---|---|
| 5,391,199 A | 2/1995 | Ben-Haim |
| 6,208,135 B1 | 3/2001 | Shattil |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,731,968 B2 | 5/2004 | Buchanan |
| 7,116,288 B2 * | 10/2006 | Shiizaki et al. ................. 345/60 |
| 7,450,996 B2 | 11/2008 | MacDonald et al. |
| 7,525,314 B1 * | 4/2009 | Heiland ........................ 324/320 |
| 7,860,553 B2 | 12/2010 | Govari et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2008/0013742 A1 | 1/2008 | Chang |
| 2008/0287803 A1 * | 11/2008 | Li et al. ......................... 600/466 |
| 2009/0269943 A1 * | 10/2009 | Palli et al. ...................... 439/39 |

FOREIGN PATENT DOCUMENTS

| | | |
|---|---|---|
| CN | 101095613 A | 1/2008 |
| EP | 0 982 597 A2 | 3/2000 |
| EP | 1 818 012 A1 | 8/2007 |

(Continued)

OTHER PUBLICATIONS

Extended European Search Report dated Oct. 11, 2012 from related European Application No. 12175271.1.

(Continued)

*Primary Examiner* — Ruth S Smith
(74) *Attorney, Agent, or Firm* — Roberts Mlotkowski Safran Cole & Calderon, P.C.

(57) ABSTRACT

An electrical connector includes one or more connector terminals, which are connected to wiring extending from the connector and are coupled to interconnect with corresponding connector terminals in a mating connector. An active shielding circuit is mounted adjacent to the connector terminals and is configured to sense a first magnetic field in a vicinity of the electrical connector and to generate, based on the sensed magnetic field, a second magnetic field that reduces interference induced in the wiring and the connector terminals by the first magnetic field.

17 Claims, 2 Drawing Sheets

(56) References Cited

FOREIGN PATENT DOCUMENTS

| | | |
|---|---|---|
| EP | 1818012 B1 | 10/2008 |
| EP | 0982597 B1 | 7/2013 |
| JP | 2005003503 A | 1/2005 |
| JP | 2010017549 A | 1/2010 |
| WO | WO 96/05768 A1 | 2/1996 |

OTHER PUBLICATIONS

European Search Report completed Oct. 4, 2012 for corresponding Patent Application No. EP12175271.

* cited by examiner

CONNECTOR WITH ACTIVE SHIELDING

FIELD OF THE INVENTION

The present invention relates generally to electrical connectors, and particularly to methods and systems for protecting connectors from magnetic interference.

BACKGROUND OF THE INVENTION

Various electronic systems operate in the presence of magnetic fields. For example, some magnetic position tracking systems track the position of a catheters or other probe in a patient body by generating known magnetic fields and measuring the fields using a magnetic field sensor fitted in the probe. Systems of this sort are described, for example, in U.S. Pat. Nos. 5,391,199, 6,690,963, 6,484,118, 6,239,724, 6,618,612 and 6,332,089, in PCT International Publication WO 96/05768, and in U.S. Patent Application Publications 2002/0065455, 2003/0120150 and 2004/0068178, whose disclosures are all incorporated herein by reference.

SUMMARY OF THE INVENTION

An embodiment of the present invention that is described herein provides an electrical connector. The electrical connector includes one or more connector terminals, which are connected to wiring extending from the connector and are coupled to interconnect with corresponding connector terminals in a mating connector. An active shielding circuit is mounted adjacent to the connector terminals and is configured to sense a first magnetic field in a vicinity of the electrical connector and to generate, based on the sensed magnetic field, a second magnetic field that reduces interference induced in the wiring and the connector terminals by the first magnetic field.

In some embodiments, the electrical connector includes a connector housing, and the connector terminals and the active shielding circuit are fitted in the connector housing. In a disclosed embodiment, the active shielding circuit includes at least one sense coil for sensing the first magnetic field, at least one generator coil for generating the second magnetic field, and drive circuitry that is configured to drive the generator coil based on the first magnetic field sensed by the sense coil.

In an embodiment, the connector terminals are arranged in a plane, and the sense coil and the generator coil are parallel to the plane. The at least one generator coil may include first and second generator coils that are located respectively on first and second opposite sides of the plane containing the connector terminals. In another embodiment, the drive circuitry includes an operational amplifier that is driven with a first current indicative of the sensed first magnetic field, and a current source that is controlled by the operational amplifier to produce a second current for driving the generator coil.

In yet another embodiment, the sense coil and the generator coil are disposed on at least one Printed Circuit Board (PCB). In still another embodiment, the active shielding circuit is matched to a frequency range of the first magnetic field. In an embodiment, the second magnetic field is equal in amplitude and opposite in polarity to the first magnetic field.

There is additionally provided, in accordance with an embodiment of the present invention, a catheter including a transducer, a cable and an electrical connector. The transducer is fitted in a distal end of the catheter, the cable exchanges electrical signals with the transducer, and the electrical connector is connected to the cable for transferring the electrical signals. The electrical connector includes one or more connector terminals and an active shielding circuit. The connector terminals are connected to wiring extending from the connector and are coupled to interconnect with corresponding connector terminals in a mating connector. The active shielding circuit is mounted adjacent to the connector terminals and is configured to sense a first magnetic field in a vicinity of the electrical connector and to generate, based on the sensed magnetic field, a second magnetic field that reduces interference induced in the wiring and the connector terminals by the first magnetic field.

There is also provided, in accordance with an embodiment of the present invention, a method including transferring one or more signals via an electrical connector, which includes one or more connector terminals that are connected to wiring extending from the connector and are coupled to interconnect with corresponding connector terminals in a mating connector. A first magnetic field is sensed in a vicinity of the electrical connector. A second magnetic field, which reduces interference induced in the signals at the wiring and the connector terminals by the first magnetic field, is generated based on the sensed magnetic field.

The present invention will be more fully understood from the following detailed description of the embodiments thereof, taken together with the drawings in which:

DETAILED DESCRIPTION OF EMBODIMENTS

Overview

Magnetic fields may cause interference to electronic systems, and in particular may distort signals that are transferred via unshielded connectors and wiring. One example scenario of this sort may occur in a magnetic positioning system that tracks the position of an intra-cardiac catheter. In such a system, the catheter is typically connected to a system console using a cable that includes at least one connector. The signals transferred by the catheter are typically weak, and may be severely distorted by the magnetic field generated by the system. This distortion may lead to erroneous position measurements.

Embodiments of the present invention that are described herein provide improved methods and devices for shielding connectors from magnetic field interference. In some embodiments, a connector comprises an active shielding circuit that is mounted adjacent to the connector terminals. The active shielding circuit senses the magnetic field in the vicinity of the connector. Based on the sensed field, the circuit generates an opposing magnetic field that reduces the interference induced in the connector terminals and wiring by the magnetic field.

Example configurations of connectors and active shielding circuits are described below. The disclosed techniques are typically simpler, lower cost and provide better shielding than passive solutions such as mu-metal shielding. Although the embodiments described herein refer to catheters and magnetic position tracking systems, the methods and devices described herein can be used for active shielding of connectors in various other systems and environments.

System Description

Figure 1:
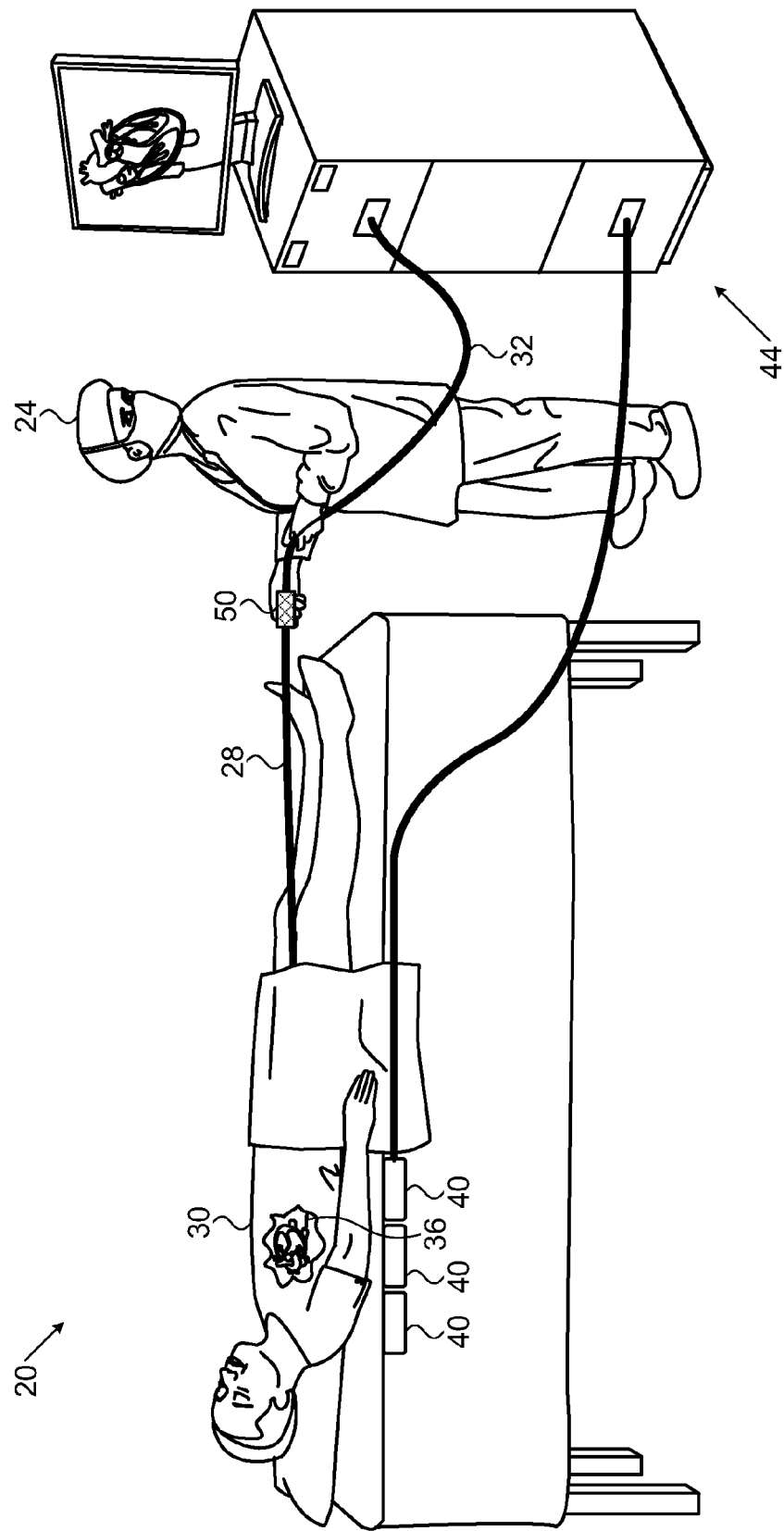
FIG. 1 is a schematic, pictorial illustration of a system for magnetic position tracking of a cardiac catheter, in accordance with an embodiment of the present invention.

FIG. 1 is a schematic, pictorial illustration of a system 20 for magnetic position tracking that uses a cardiac catheter, in accordance with an embodiment of the present invention. System 20 may be based, for example, on the CARTO™ system, produced by Biosense-Webster Inc. (Diamond Bar, Calif.). In system 20, a physician 24 inserts a catheter 28 into the body of a patient 30. Catheter 28 has a proximal end that is handled by the physician, and a distal end 36 that is navigated through the patient body. Catheter 28 is connected to a control console 44 using a cable 32.

One or more field-generating coils 40, which are controlled by console 44, generate Alternating Current (AC) magnetic fields in the vicinity of the patient. A magnetic field sensor or other transducer (not shown) fitted in distal end 36 of catheter 28 senses the magnetic fields and generates electrical signals in response to the sensed fields. The electrical signals are transferred from the distal end of the catheter via cable 32 to console 40, and the console calculates and displays the position of the catheter distal end by processing the signals. Systems of this sort are described in detail in the above-cited references.

In some embodiments, catheter 28 is connected to cable 32 using a pair of mating electrical connectors 50. In many practical cases, the electrical signals traversing connectors 50 may be distorted by the magnetic fields that are generated by coils 40 (sometimes referred to as "external magnetic field"). This distortion may in turn introduce errors into the position calculations carried out by console 44. In some embodiments, one of connectors 50 comprises an active shielding circuit that reduces the interference caused by the magnetic fields.

Figure 2:
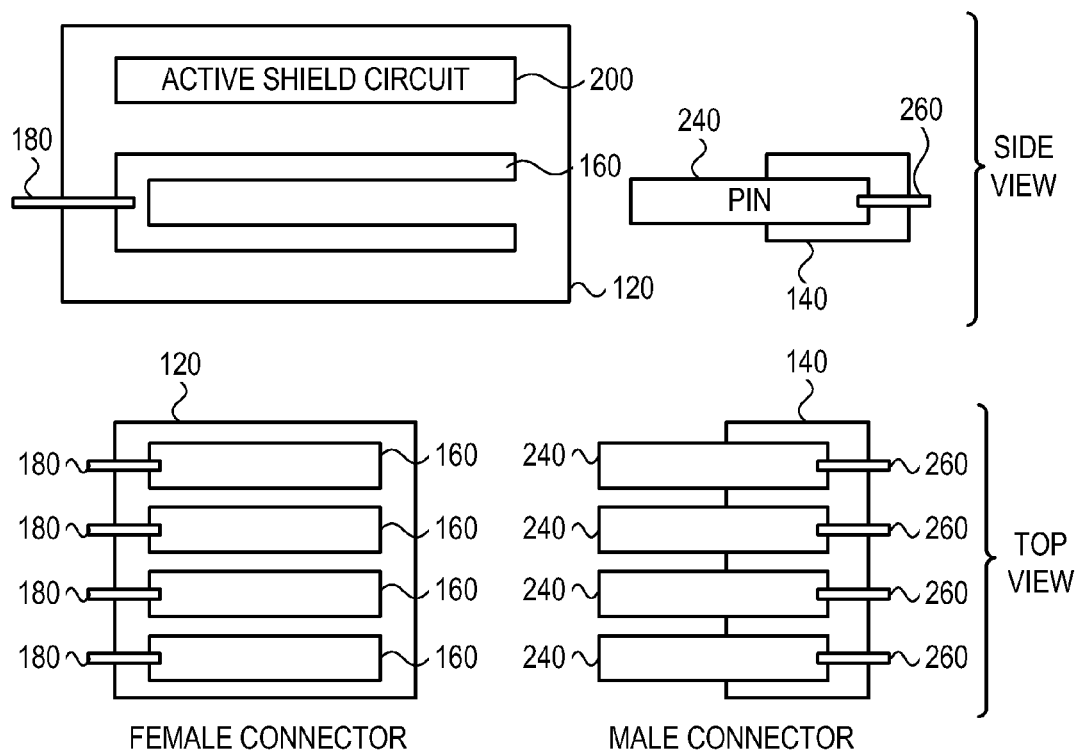
FIG. 2 is a diagram that schematically illustrates a pair of connectors with active shielding, in accordance with an embodiment of the present invention.

FIG. 2 is a diagram that schematically illustrates side and top views of a pair of connectors that use active shielding, in accordance with an embodiment of the present invention. These connectors can be used, for example, for implementing connectors 50 of FIG. 1 above.

In the present example, the pair of connectors comprises a female connector that is shown on the left-hand side of the figure, and a male connector that is shown on the right-hand side. The top and bottom parts of the figure show side and top views of the connectors, respectively.

The female connector comprises a connector housing 120 and one or more sockets 160. Wiring 180 is connected to sockets 160 and extend from housing 120, for transferring electrical signals to and/or from the sockets. The male connector comprises a connector housing 140 and one or more pins 240. Wiring 260 is connected to pins 240 and extend from housing 140, for transferring electrical signals to and/or from the pins. An active shielding circuit 200, which is described in detail below, is mounted in housing 120 of the female connector adjacent to sockets 160.

When the male connector plugs into the female connector, pins 240 plug into sockets 160. The pin-socket connection area is in close proximity to active circuit 200, and therefore cancellation of magnetic fields by circuit 200 effectively reduces the magnetic field interference in this area. Thus, the electrical signals that are transferred via the connectors are effectively protected from magnetic field interference.

In the present context, both pins 240 and sockets 160 are referred to herein as connector terminals. Although in the present example circuit 200 is mounted in the female connector, in alternative embodiment the active shielding circuit may be mounted in the male connector. Although the present example refers to male and female connectors, the disclosed techniques can also be used in hybrid connectors having any suitable mix of one or more pins and one or more sockets. Furthermore, the disclosed techniques can be used with connectors having any other suitable kind of connector terminals.

Figure 3:
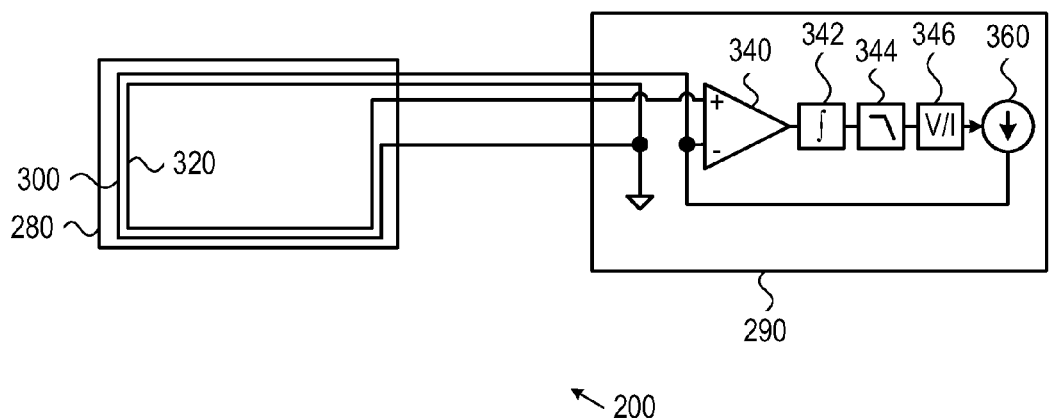
FIG. 3 is a circuit diagram which schematically describes an active shielding circuit, in accordance with embodiments of the present invention.

FIG. 3 is a circuit diagram that schematically illustrates active shielding circuit 200, in accordance with an embodiment of the present invention. In the embodiment of FIG. 3, circuit 200 comprises a coil circuit 280 and a driver circuit 290, which may be fabricated on a single circuit board or on separate circuit boards.

Coil circuit 280 comprises a sense coil 320 and a generator coil 300. Sense coil 320 senses the magnetic field in the vicinity of the connector. Based on the sensed magnetic field, driver circuit 290 drives generator coil 300 so as to generate an opposing magnetic field that counteracts the sensed magnetic field. In other words, coil 300 generates an opposing magnetic field that cancels (or at least considerably reduces) the magnetic field sensed by coil 320. As a result, the net magnetic field that affects the connector terminals and wiring is canceled or considerably reduced.

In the present example, the connector terminals are arranged in a planar configuration, and coils 300 and 320 are planar and parallel to the plane of the connector terminals. This configuration is useful for canceling magnetic fields that are perpendicular to the plane of the connector terminals, which are often dominant in causing interference. The sense and generator coils may be disposed on a miniature Printed Circuit Board (PCB) that is mounted inside the connector housing adjacent to the connector terminals.

In alternative embodiments, any other suitable configuration of connector terminals, one or more sense coils and one or more generator coils can be used. For example, the active shielding circuit may comprise two generator coils 300, one on either side of the plane of the connector terminals, in a Helmholtz configuration.

In some embodiments, drive circuit 290 comprises an operational amplifier 340 that is connected in a negative feedback configuration. The output of operational amplifier 340 is integrated by an integrator 342. A Low-Pass Filter (LPF) 344 filters the output of integrator 342. In some embodiments, integrator 342 and LPF 344 may be implemented as a single filter. A Voltage-to-Current (V/I) converter converts the voltage at the output of LPF 344 into current, and drives a current source 360.

One terminal of sense coil 320 and one terminal of generator coil 300 are connected to ground. The other terminal of sense coil 320 and the other terminal of generator coil 300 are connected to the positive input of operational amplifier 340. The other terminal of generator coil 300 is connected to the negative input of amplifier 340. Current source 360 injects current to generator drive coil 300, at the terminal that is connected to the negative input of the operational amplifier.

Operational amplifier 340 is arranged in a negative feedback configuration. The equilibrium state of the amplifier occurs when the magnetic field induced by generator coil 300 cancels the external magnetic field, such that the current through sense coil 320 is zero. The current induced in sense coil 320 comprises the sum of the current induced by the external magnetic field, and the current induced by the opposing magnetic field generated by generator coil 300.

In equilibrium state and with an ideal operational amplifier, the two fields are identical but have opposite polarities, and therefore cancel one another as their sum is zero. With practical operational amplifiers, the sum of the fields may not be exactly zero, and the magnetic field interference may therefore be significantly reduced but not completely cancelled.

A small change in the external magnetic field typically causes a temporary change in the current through sense coil 320, to a non-zero value. Since the sense coil is connected to a high-impedance input of operational amplifier 340, such a change in current typically changes the voltage on the positive terminal of the operational amplifier, which in turn changes the current drive of current source 360. The change in the current changes the opposing magnetic field generated by generator coil 300, and this change compensates for the change in the external magnetic field, returning the circuit to equilibrium.

The configuration of connector pair 50 and of circuit 200 shown in FIGS. 2 and 3 are example configurations, which are shown purely for the sake of conceptual clarity. In alternative embodiments, any other suitable configurations can also be used.

In some embodiments, driver circuit 290 and/or coil circuit 280 may be matched (e.g., designed for and/or tuned) to the frequency range of the external magnetic field. In some embodiment, an active shielding circuit such as circuit 200 may be used in combination with passive shielding. Although the embodiments described herein mainly address active shielding of connectors, the methods and systems described herein can also be used in other applications, such as in shielding of electronic circuit boards, integrated circuits and cables.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. An electrical connector, comprising:
   a connector housing;
   one or more connector terminals fitted within the connector housing, which are connected to wiring extending from the connector housing and are coupled to interconnect with corresponding connector terminals in a mating connector; and
   an active shielding circuit, mounted adjacent to the one or more connector terminals within the connector housing and is configured to sense a first magnetic field in a vicinity of the electrical connector and to generate, based on the sensed magnetic field, a second magnetic field that reduces interference induced in the wiring and the one or more connector terminals by the first magnetic field, the active shielding circuit comprising:
      at least one sense coil for sensing the first magnetic field;
      at least one generator coil for generating the second magnetic field; and
      a drive circuit comprising:
         an operational amplifier receiving a first input from a terminal of the at least one sense coil and a second input from a terminal of the at least one generator coil, the operational amplifier capable of amplifying a difference between the first input and the second input;
         an integrator receiving an amplified signal from the operational amplifier, the integrator capable of integrating the amplified signal;
         a low-pass filter receiving the integrated signal from the integrator, the low-pass filter capable of filtering the integrated signal;
         a voltage-to-current (V/I) converter receiving the filtered signal from the low-pass filter, the V/I converter capable of converting a voltage of the filtered signal to a current signal; and
      a current source receiving the current signal from V/I converter, the current source driving the at least one generator coil.

2. The electrical connector according to claim 1, wherein the one or more connector terminals are arranged in a plane, and wherein the at least one sense coil and the at least one generator coil are parallel to the plane.

3. The electrical connector according to claim 2, wherein the at least one generator coil comprises first and second generator coils located respectively on first and second opposing sides of the plane containing the one or more connector terminals.

4. The electrical connector according to claim 1, wherein the at least one sense coil and the at least one generator coil are disposed on at least one Printed Circuit Board (PCB).

5. The electrical connector according to claim 1, wherein the active shielding circuit is matched to a frequency range of the first magnetic field.

6. The electrical connector according to claim 1, wherein the second magnetic field is equal in amplitude and opposite in polarity to the first magnetic field.

7. The electrical connector according to claim 1, wherein the drive circuit is matched to a frequency range of an external magnetic field.

8. The electrical connector according to claim 1, wherein a coil circuit comprising the at least one sense coil and the at least one generator coil is matched to a frequency range of an external magnetic field.

9. A catheter, comprising:
   an elongated hollow shaft having a proximal end and a distal end;
   a transducer fitted in the distal end of the hollow shaft;
   a cable for exchanging electrical signals with the transducer; and
   an electrical connector connected to the cable for transferring the electrical signals, the electrical connector comprising:
      a connector housing,
      one or more connector terminals fitted within the connector housing, which are connected to wiring extending from the connector housing and are coupled to interconnect with corresponding one or more connector terminals in a mating connector, and
      an active shielding circuit mounted adjacent to the one or more connector terminals within the connector housing and is configured to sense a first magnetic field in a vicinity of the electrical connector and to generate, based on the sensed magnetic field, a second magnetic field that reduces interference induced in the wiring and the one or more connector terminals by the first magnetic field, the active shielding circuit comprising:

at least one sense coil for sensing the first magnetic field;

at least one generator coil for generating the second magnetic field; and a drive circuit comprising:

an operational amplifier receiving a first input from a terminal of the at least one sense coil and a second input from a terminal of the at least one generator coil, the operational amplifier capable of amplifying a difference between the first input and the second input;

an integrator receiving an amplified signal from the operational amplifier, the integrator capable of integrating the amplified signal;

a low-pass filter receiving the integrated signal from the integrator, the low-pass filter capable of filtering the integrated signal;

a voltage-to-current (V/I) converter receiving the filtered signal from the low-pass filter, the V/I converter capable of converting a voltage of the filtered signal to a current signal; and a current source receiving the current signal from V/I converter, the current source capable of driving the at least one generator coil.

10. A method, comprising:

transferring one or more signals via an electrical connector having a connector housing comprising one or more connector terminals fitted within the connector housing that are connected to wiring extending from the connector housing and are coupled to interconnect with corresponding one or more connector terminals in a mating connector;

sensing within the connector housing a first magnetic field in a vicinity of the electrical connector, sensing the first magnetic field comprising measuring the first magnetic field using at least one sense coil;

producing an amplified signal by amplifying a difference between a current in the at least one sense coil and a current in at least one generator coil;

producing an integrated signal by integrating the amplified signal;

producing a filtered signal by filtering the integrated signal;

converting a voltage of the filtered signal to a current signal to drive a current source that injects current into the at least one generator coil; and generating with the at least one generator coil a second magnetic field that reduces interference induced in the signals at the wiring and the one or more connector terminals by the first magnetic field, the second magnetic field based on the sensed magnetic field.

11. The method according to claim 10, wherein the one or more connector terminals are arranged in a plane, and wherein the at least one sense coil and the at least one generator coil are parallel to the plane.

12. The method according to claim 11, wherein generating the second magnetic field comprises producing the second magnetic field using first and second generator coils located respectively on first and second opposing sides of the plane containing the one or more connector terminals.

13. The method according to claim 10, wherein the at least one sense coil and the at least one generator coil are disposed on at least one Printed Circuit Board (PCB).

14. The method according to claim 10, wherein sensing the first magnetic field and generating the second magnetic field comprise operating circuitry matched to a frequency range of the first magnetic field.

15. The method according to claim 10, wherein the second magnetic field is equal in amplitude and opposite in polarity to the first magnetic field.

16. The method according to claim 10, wherein the production of the amplified signal, production of the integrated signal, production of the filtered signal, and conversion of the voltage of the filtered to the current signal are performed within a circuit matching a frequency range of an external magnetic field.

17. The method according to claim 10, further comprising matching a frequency of a coil circuit comprising the at least one sense coil and the at least one generator coil to a frequency range of an external magnetic field.

* * * * *